United States Patent
Hedengren et al.

[11] Patent Number: 5,418,457
[45] Date of Patent: May 23, 1995

[54] SYSTEM AND METHOD FOR ALIGNING AN INSPECTION PROBE AND MAINTAINING UNIFORM SPACING BETWEEN THE PROBE SURFACE AND AN INSPECTION SURFACE

[75] Inventors: Kristina H. V. Hedengren, Schenectady; John D. Young, Rexford, both of N.Y.

[73] Assignee: General Electric Company, Schenectady, N.Y.

[21] Appl. No.: 31,303

[22] Filed: Mar. 12, 1993

[51] Int. Cl.$^6$ .................... G01N 27/72; G01N 27/82; G01R 33/00
[52] U.S. Cl. .................... 324/225; 324/227; 324/238
[58] Field of Search .............. 324/225, 226, 227, 232, 324/234–243

[56] References Cited

U.S. PATENT DOCUMENTS

| | | | |
|---|---|---|---|
| 4,641,092 | 2/1987 | Sakamoto et al. | 324/225 |
| 4,675,502 | 6/1987 | Haefner et al. | 219/124.34 |
| 4,783,695 | 11/1988 | Eichelberger et al. | 357/65 |
| 4,843,318 | 6/1989 | Greenblatt et al. | 324/227 |
| 4,849,693 | 7/1989 | Prince et al. | 324/227 |
| 5,161,413 | 11/1992 | Junker et al. | 73/634 |
| 5,182,513 | 1/1993 | Young et al. | 324/232 |

Primary Examiner—Walter E. Snow
Attorney, Agent, or Firm—David C. Goldman; Paul R. Webb, II

[57] ABSTRACT

A system and method is provided for aligning a scanning surface of an inspection probe relative to a workpiece surface under inspection. The probe preferably includes at least three alignment eddy current elements, each producing a respective spacing indication electrical signal in accordance with a spacing between each alignment eddy current element and the workpiece. The system further comprises processing means which receives each spacing-indication electrical signal so as to generate data indicative of the relative alignment between the scanning surface of the probe and the workpiece surface. A controller is responsive to the alignment data for aligning the probe such that in operation the scanning surface thereof is substantially parallel relative to the workpiece surface. The probe can include inspection eddy current elements, in which case the alignment and the inspection eddy current elements can be fabricated to form an integral eddy current inspection probe.

15 Claims, 4 Drawing Sheets

SYSTEM AND METHOD FOR ALIGNING AN INSPECTION PROBE AND MAINTAINING UNIFORM SPACING BETWEEN THE PROBE SURFACE AND AN INSPECTION SURFACE

BACKGROUND OF THE INVENTION

This invention relates to a system and method for aligning a scanning surface of an inspection probe relative to a workpiece surface being inspected by the probe. More particularly, the present invention relates to a system employing eddy current elements for providing substantial parallel alignment between the scanning surface of the inspection probe and the workpiece surface under inspection.

In industrial non-destructive inspection operations which typically employ inspection probes, such as for example eddy current or ultrasonic probes or the like, for detection of flaws in a workpiece under inspection, it is highly desirable to use techniques which can effectively reduce the time and cost required to inspect a workpiece without compromising the quality of the inspection operation. Implementing such effective techniques becomes particularly difficult when the workpiece to be inspected has a large surface area (e.g., the skin of an aircraft wing) which must be thoroughly inspected not only to detect microscopic flaws therein but also to pinpoint the location of the detected flaws.

To address the need for effective inspection techniques, inspection probes have been proposed which provide an increased scanning surface area so as to speed up the inspection operation. A typical approach employed in the fabrication of these proposed inspection probes is to spatially correlate a plurality of elementary inspection elements over the scanning surface of the probe. This approach can provide an array of inspection elements which not only has an increased scanning surface area but also has the resolution and sensitivity required to accurately and precisely detect and locate microscopic flaws in the workpiece under inspection.

For instance, probes used in eddy current inspection may thus comprise a plurality of inspection eddy current elements arrayed throughout the scanning surface of the probe. Although impressive improvements have been made with the use of such proposed eddy current probes, significant problems remain. For example, undesirable electrical signals can arise during routine eddy current inspections due to variations in the spacing between each inspection eddy current element and the underlying surface of the workpiece undergoing inspection. This phenomenon is generally referred to as the lift-off effect, a term of art used to characterize the undesirable signals which result from the spacing variations. The lift-off effect is capable of corrupting actual eddy current measurement signals to the point of dangerously concealing the presence of actual flaws in the workpiece under inspection. Accordingly, the lift-off effect can significantly impair eddy current inspection operations and can jeopardize the reliable use of such proposed eddy current probes (e.g., probes using an array of inspection eddy current elements) since their ability to reliably and accurately detect flaws in the workpiece is diminished. Similar undesirable effects, due to spacing variations between the scanning surface and the workpiece surface, can also affect other kinds of inspection probes, such as for example ultrasonic inspection probes. Moreover, inspection of workpieces having a substantially curved surface, for example, remains especially troublesome due to the lift-off effect since it is particularly difficult to maintain a uniform relationship between the inspection elements arrayed over the scanning surface of the probe and the workpiece surface.

It is therefore desirable to provide a system and method for aligning the scanning surface of the probe so as to maintain uniform spacing between each inspection element therein and the surface under inspection. Maintaining such uniform spacing therebetween would eliminate erroneous indications resulting from variations in the spacing between each of the individual inspection elements and the workpiece being inspected.

A known typical system employed to align the scanning surface of inspection probes may use a controller which uses a priori information about the shape of a generic workpiece surface. For instance, a scan plan of the generic workpiece surface can be programmed off-line and stored in the controller prior to starting the inspection operation. This known system, however, has several disadvantages since the a priori information stored in the controller generally cannot take into account dimensional tolerances between the numerous workpieces being inspected in a production environment, and therefore this system is usually unable to provide the continuous alignment required to substantially reduce erroneous indications due to the lift-off effect. Moreover, this known system in general requires additional off-line programming to align the inspection probe over workpieces having a geometry different from the chosen generic workpiece.

OBJECTS OF THE INVENTION

It is an object of the present invention to provide a new and improved system and method for aligning the scanning surface of an inspection probe, such as an eddy current probe, relative to a workpiece surface under inspection.

Another object of the present invention is to provide uniform spacing between the scanning surface of an inspection probe and the workpiece under inspection.

A further object of the present invention is to automatically or manually align the scanning surface of an inspection probe which in operation advances over the workpiece under inspection.

SUMMARY OF THE INVENTION

The above and further objects of the present invention will become apparent as the description proceeds. In accordance with the present invention, a system is provided for providing continuous and substantially parallel alignment between a scanning surface of an inspection probe, such as for example an eddy current probe or an ultrasound probe, and a workpiece surface under inspection. In the particular case of an integral eddy current inspection probe, a plurality of inspection eddy current elements can be arrayed throughout the scanning surface thereof. Each of the inspection eddy current elements have means disposed in at least one layer of a multilayer, integral structure for producing a respective electrical signal indicative of a discontinuity in the workpiece when positioned adjacent thereto. In a preferred embodiment of the invention the inspection probe includes at least three alignment eddy current elements noncollinearly positioned with respect to one another and being mutually spaced at a predetermined distance from one another over the scanning surface of the probe. Each of the alignment eddy current elements has means disposed in at least one layer of the multi-layer structure for producing a respective electrical signal in accordance with a spacing between each alignment eddy current element and the workpiece surface. The alignment eddy current elements in combination with the inspection eddy current elements can form an integral eddy current inspection probe.

The system further comprises processing means, such as a signal processor, connected to each alignment element to receive and to process the spacing-indication electrical signals so as to generate data indicative of the relative alignment between the scanning surface of the probe and the workpiece surface, in accordance with the processed electrical signals. In one aspect of the invention, a controller connected to the signal processor is responsive to the alignment data for aligning the probe such that in operation the scanning surface thereof is automatically aligned substantially parallel relative to the workpiece surface.

In another embodiment of the invention at least a pair of associated alignment eddy current elements can be positioned on opposite sides of the probe on a predetermined axis which traverses the scanning surface of the probe. Each electrical signal of the associated pair of alignment eddy current elements may be connected to a differential amplifier to be received and processed so as to generate a difference signal representing the difference of the received electrical signals. The difference signal may be connected to display means for providing visual indicia of the relative alignment between at least the traversing axis and the workpiece surface. In one feature of the invention, the multi-layer integral structure can be flexible, thereby providing a substantially flexible eddy current probe which can be accommodated in a housing having a predetermined shape substantially conformable to the workpiece. In accordance with this feature of the invention, the system is capable of providing substantial uniform relationship between the inspection eddy current elements and a substantially curved workpiece surface. In yet another aspect of the invention, the inspection and alignment eddy current elements can be respectively patterned and electrically interconnected within the flexible structure, preferably using a photolithographic process.

BRIEF DESCRIPTION OF THE DRAWINGS

The features of the present invention believed to be novel are set forth with particularity in the appended claims. The invention itself, both as to organization and method of operation, together with further objects and advantages thereof, may best be understood by reference to the following description in conjunction with the accompanying drawings in which like numerals represent like parts throughout the drawing, and in which:

DETAILED DESCRIPTION OF THE INVENTION

Figure 1:
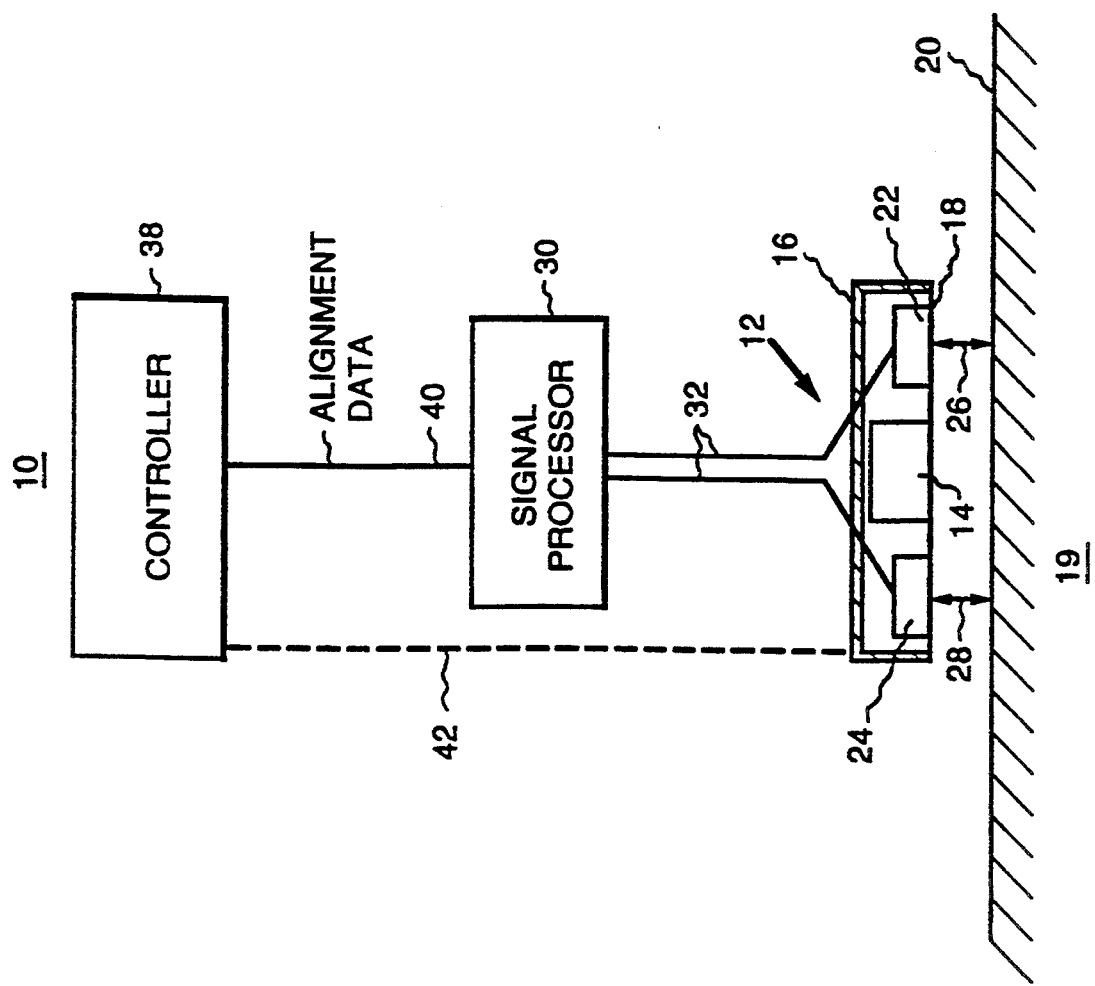
FIG. 1 shows a schematic of the system of the present invention, including a side elevation view of an exemplary eddy current probe used therein.

FIG. 1 shows the system 10 of the present invention using, by way of example and not by way of limitation, an eddy current inspection probe 12 which includes at least one inspection eddy current element (e.g., 14) enclosed within a housing 16 and located on the scanning surface 18 of the probe 12. The inspection eddy current element 14 cooperates with at least one associated drive coil (not shown) electrically connected to an appropriate electrical current source for establishing an inducing time-varying magnetic field in a manner well understood by those skilled in the art. The inducing magnetic field establishes an eddy current flow in a workpiece under inspection (e.g., 19) and the eddy current flow in turn establishes a reflected magnetic field. The presence of a discontinuity, such as a flaw, a crack or other irregularity, in the workpiece under inspection causes a disruption to the eddy current flow in the vicinity of the discontinuity, and changes the reflected magnetic field. The change to the reflected magnetic field causes inspection eddy current element 14 to produce a respective electrical signal indicative of the discontinuity when positioned adjacent to the workpiece.

As would be readily understood by those skilled in the art, the inspection eddy current element 14 is, in general, susceptible to the lift-off effect which, as previously described, can produce undesirable signals due to variations in the spacing between the inspection eddy current element and an underlying workpiece surface 20. For simplicity of illustration, FIG. 1 illustrates only one inspection eddy current element; it should be appreciated, however, that in general the probe 12 can include a plurality of inspection eddy current elements arrayed throughout scanning surface 18. Accordingly, if the scanning surface 18 of probe 12 is not substantially parallel to the workpiece surface 20, then the inspection eddy current elements (e.g., 14) being subjected to different lift-off effects would not provide precise indications of discontinuities in the workpiece.

In the embodiment shown in FIG. 1, the probe 12 further includes alignment eddy current elements (e.g., 22 and 24) located by way of example on the scanning surface of probe 12. It should be appreciated that other arrangements for the alignment eddy current elements can be equally effective so long as they have a predetermined spatial registration with respect to the scanning surface 18. For instance, alignment eddy current elements 22 and 24 could be supported outside probe 12 flush with scanning surface 18. Similar to the inspection eddy current elements, each alignment eddy current element cooperates with an associated drive coil (not shown) for establishing an inducing time-varying magnetic field. It will be appreciated that in the particular case of an eddy current inspection probe (i.e., a probe which comprises eddy current elements both for inspection and for alignment, as exemplified in FIG. 1) the associated drive coils may be conveniently shared by both the inspection and the alignment elements. Each alignment eddy current element (e.g., 22 and 24) is adapted to produce a respective spacing-indication electrical signal indicative of a spacing (e.g., 26 and 28) between each respective alignment eddy current element and the workpiece surface 20.

Figure 2:
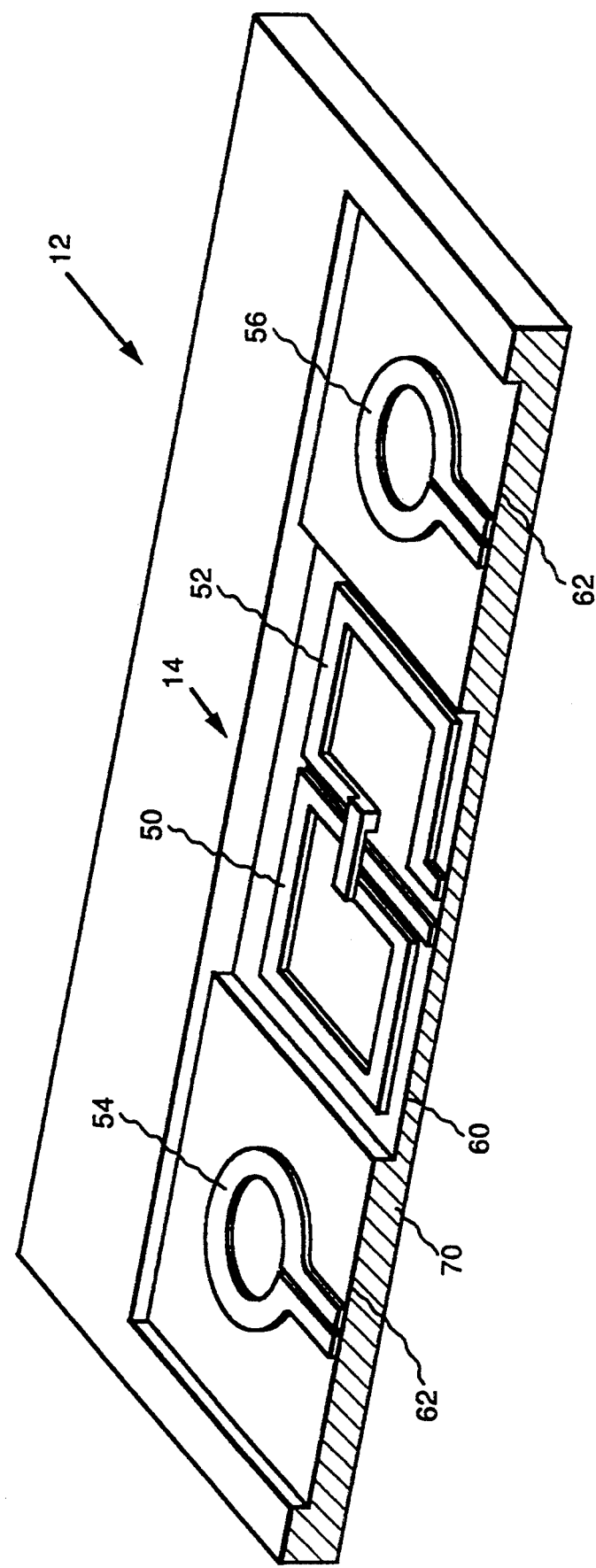
FIG. 2 shows a perspective view of a typical multi-layer structure used in one embodiment of the eddy current probe shown in FIG. 1.

FIG. 2 shows details about typical inspection and alignment eddy current elements which can be used in one embodiment of the inspection probe 12 shown in FIG. 1. As illustrated in FIG. 2, each inspection eddy current element (e.g., 14) can include one or more sense coils (e.g., 50 and 52) disposed in at least one layer (e.g., 60) of a multi-layer integral structure 70. Each sense coil comprises a metallized pattern electrically responsive so as to produce the electrical signals indicative of discontinuities in the workpiece. Preferably, each inspection eddy current element operates in a differential mode, that is, each inspection eddy current element has its respective sense coils interconnected (as illustrated in FIG. 2) to produce an electrical signal which is the difference of the individual responses of such respective sense coils. The interconnection is in a layer not shared by sense coils 50 and 52 to avoid undesirable electrical shorts. FIG. 2 also illustrates typical alignment eddy current elements (e.g., 54 and 56) disposed in at least one layer (e.g., 62) of the multi-layer structure 70. Preferably each alignment eddy current element operates in an absolute mode, that is, each alignment eddy current element has its respective sense coil connected to produce an electrical signal suitable to indicate dimensional variations relative to the workpiece surface.

FIG. 1 further shows a signal processor 30 connected to each alignment eddy current element (e.g., 22 and 24) by a set of electrical leads 32 to receive each respective spacing-indication electrical signal produced by each alignment eddy current element. The signal processor may be similar to the multichannel eddy current data acquisition system described in U.S. Pat. No. 5,182,513 entitled "Method and Apparatus for a Multichannel Multifrequency Data Acquisition System for Nondestructive Eddy Current Inspection Testing" by J. D. Young et al., assigned to the assignee of the present invention and hereby incorporated by reference. The signal processor processes each of the spacing-indication electrical signals received from each alignment eddy current element and spatially correlates the received signals to generate real time data indicative of the alignment between the scanning surface 18 and the workpiece surface 20.

The alignment data is supplied to a controller 38 by means of a data bus 40 connected to the signal processor 30. The controller 38 (which may be of the kind described in U.S. Pat. No. 4,675,502 entitled "Real Time Tracking Control for Taught Path Robots", by K. B. Haefner et al., assigned to the assignee of the present invention and hereby incorporated by reference) is responsive to the alignment data to generate servo commands automatically controlling an electromechanical linkage such as, for example, a robotic arm or the like (schematically represented by heavy dashed line 42) mechanically connected to housing 16. In particular, the electromechanical linkage 42 can manipulate the housing so that in operation the scanning surface 18 of the inspection probe 12 is substantially parallel relative to the workpiece surface 20.

Figure 3:
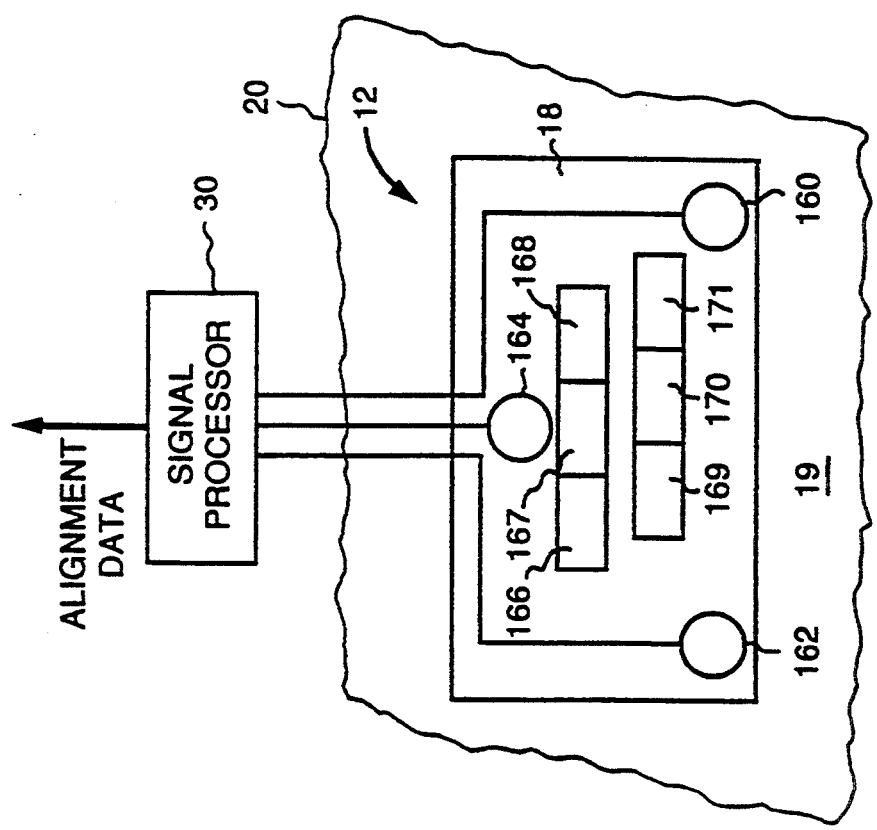
FIG. 3 shows a schematic of one embodiment of the present invention, including a top plan view of the eddy current elements used therein.

FIG. 3 shows a preferred embodiment of the present invention wherein at least three alignment eddy current elements 160, 162 and 164 are noncollinearly positioned with respect to one another throughout the scanning surface of probe 12. Such positioning ensures that the alignment data, after being processed by the signal processor 30, provides the information required to achieve substantial parallel alignment between a plurality of inspection eddy current elements 166–171 (shown in FIG. 2 as being two-dimensionally arrayed on the scanning surface 18) and workpiece surface 20. The alignment eddy current elements 160, 162, 164 are positioned in mutually spaced relationship at a predetermined distance from one another, such predetermined distances being typically chosen according to the actual dimensions of the scanning surface.

Figure 4:
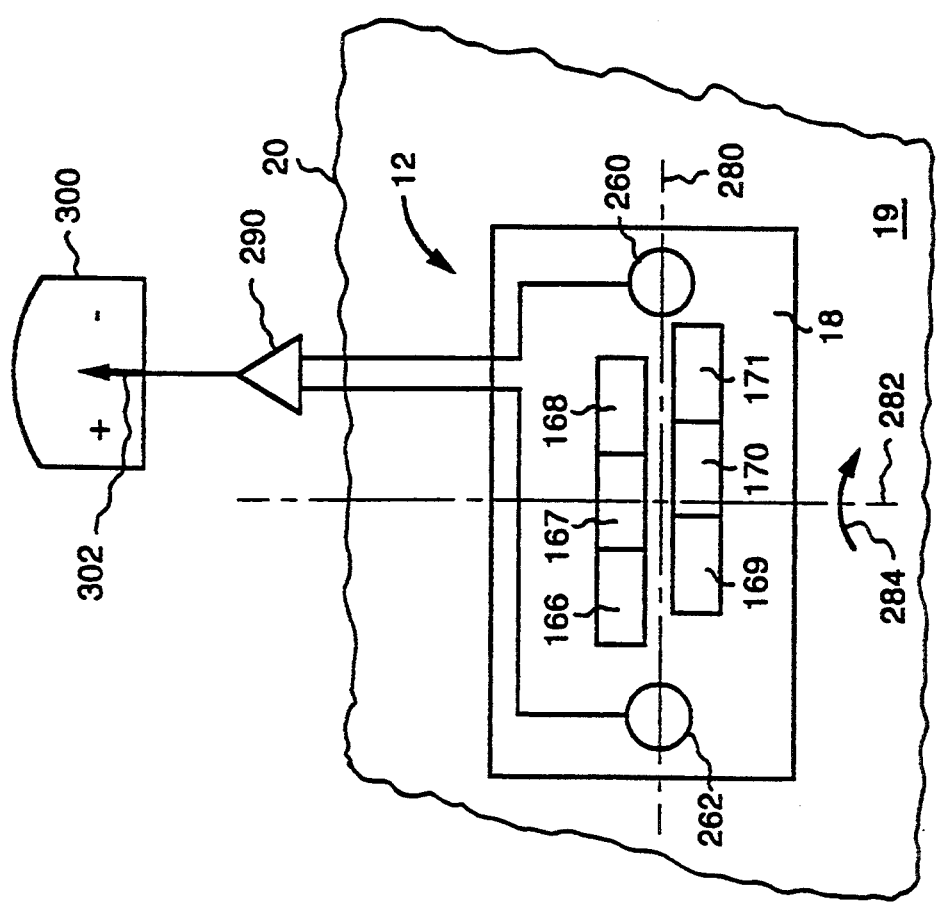
FIG. 4 shows a schematic of another embodiment of the present invention, including a top plan view of the eddy current elements used therein.

FIG. 4 illustrates an alternate embodiment which can be used in certain situations where manual operation is sufficient to provide a desired alignment between the scanning surface 18 of inspection probe 12 and the workpiece surface 20. FIG. 4 shows an embodiment wherein the inspection probe 12 includes at least an associated pair (e.g., 260 and 262) of alignment eddy current elements positioned on opposite sides of probe 12 on a predetermined axis (e.g 280) traversing the scanning surface 18. FIG. 4 further illustrates that the signal processing of the spacing-indication electrical signals can be performed by means of a conventional differential amplifier 290 connected to receive the spacing-indication electrical signals produced by the associated pair of alignment eddy current elements. The differential amplifier generates a difference signal which represents the difference of the received spacing-indication electrical signals and constitutes at least a portion of the alignment data. FIG. 4 further illustrates display means such as a meter 300 connected to the differential amplifier 290 to receive the difference signal and capable of providing visual indicia based on the received difference signal of the relative alignment between at least the traversing axis (e.g, 280) and the workpiece surface 20. This embodiment may be conveniently used in situations where the probe 12 may be pivotally supported along a pivot axis (e.g., 282) substantially perpendicular to the traversing axis 280 and thus the difference signal provides sufficient information to achieve parallel alignment between the scanning surface 18 and the workpiece surface 20. For instance, if probe 12 is rotated about pivot axis 282 in the direction shown by arrow 284, alignment eddy current element 260 would be closer to the workpiece surface 20 than alignment eddy current element 262 and therefore the spacing-indication electrical signals from the associated alignment eddy current element pair 260 and 262 would not be the same. Accordingly, meter 300 would provide an indication, for example, indicator 302 could deviate from a center position toward the positive sign. Corrective action could then be taken, for example, probe 12 could be rotated about pivot axis 282 opposite to the direction indicated by arrow 284 until indicator 302 becomes centered. Similar implementation can also be used in the embodiment shown in FIG. 3. For example, the signal processor 30 illustrated in FIG. 3 may be replaced by a set of differential amplifiers connected to respective associated pairs of the alignment eddy current elements therein.

Figure 5:
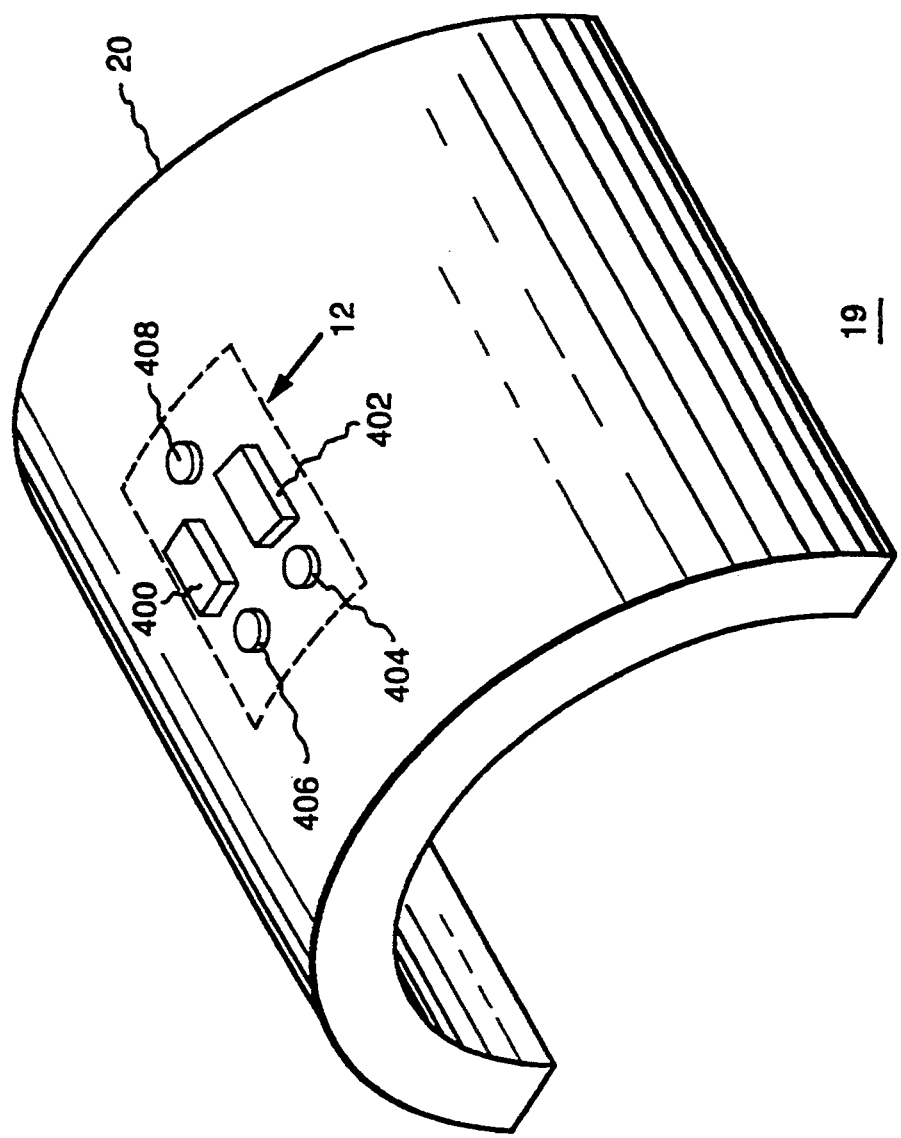
FIG. 5 shows a perspective view of a portion of a workpiece having a substantially curved surface being inspected in accordance with a feature of the present invention.

FIG. 5 illustrates a feature of the invention which permits substantial parallel alignment of the scanning surface of probe 12 relative to a workpiece 19 having a substantially curved workpiece surface 20. In accordance with this feature of the invention, the inspection probe 12 may be fabricated according to a process (as will be explained shortly hereafter) which can provide a flexible inspection probe. As illustrated in FIG. 5, such a flexible inspection probe may be accommodated in a housing (schematically represented by the dashed enclosure) having a predetermined shape being selected so that the scanning surface of the probe is substantially conformable to the geometry of the workpiece surface. In cooperation with the electromechanical linkage 42 (schematically illustrated in FIG. 1) the probe 12 can be aligned so that the inspection eddy current elements remain substantially equidistant from the underlying surface 20. The flexible inspection probe 12 may be of the kind but not limited to, for example, an eddy current probe fabricated using a photolithographic process as disclosed in U.S. Pat. No. 4,783,695 entitled "Multichip Integrated Circuit Packaging Configuration and method" by C. W. Eichelberger et al. The above patent are assigned to the assignee of the present invention and hereby incorporated by reference.

The referred HDI technique allows the fabrication of an eddy current probe comprising fully integrated flexible, miniaturized inspection eddy current elements (e.g., 400 and 402) and alignment eddy current elements (e.g., 404, 406, 408) having a precisely matched electrical response not generally feasible with conventional eddy current elements, e.g., eddy current elements using mechanically wound coils. Description of such HDI fabricated eddy current probe is provided in U.S. patent application Ser. No. 07/696,455 entitled "Flexible Eddy Current Surface Measurement Array For Detecting Near Surface Flaws in A Conductive Part" by K. H. Hedengren et. al., filed May 6, 1991, now U.S. Pat. No. 5,389,876, assigned to the assignee of the present invention and hereby incorporated by reference. Briefly, the referred HDI technique comprises metallizing, patterning and etching steps which advantageously allow the probe 12 to have its integral multi-layer structure (illustrated in FIG. 2) to be flexible, as well as constructed with precision and uniformity. Each inspection and alignment eddy current element typically comprises a metallized pattern which can be situated in at least one layer of a flexible structure which contains a substrate; such as Kapton ™, a polymide available from E. I. Dupont de Nemours Company. This metallized pattern is accomplished by first metallizing the flexible substrate, using sputtering or electroplating techniques to deposit thereon a coating of titanium and copper, for example. Then the patterning step, accomplished with a suitable photoresist, exposes by irradiation the metallized pattern which comprises each respective eddy current element. Thereafter, the etching step erodes away all metal but the patterned eddy current elements and associated interconnections. The above HDI technique, provided as an example of a photolithographic process and not by way of limitation, can provide an integral eddy current inspection probe comprising respective inspection and alignment eddy current elements having a level of precision heretofore unattainable by conventional means.

It will be understood that the features of the invention shown and described herein are exemplary only. Numerous variations, changes, substitutions and equivalents will now occur to those skilled in the art without departing from the spirit and scope of the present invention. Accordingly, it is intended that all subject matter described herein and shown in the illustrative drawings be regarded as illustrative only and not in a limiting sense and that the scope of the invention claimed be determined solely by the appended claims.

What is claimed is:

1. A system for providing continuous and substantially parallel alignment between a scanning surface of an inspection probe and a workpiece surface under inspection, said system comprising:
    eddy current inspection means located in said scanning surface for establishing an eddy current flow in the workpiece, a disruption in the eddy current flow therefrom representing a discontinuity, said eddy current inspection means having means for producing a respective electrical signal indicative of the discontinuity in said workpiece when positioned adjacent to said workpiece;
    eddy current alignment means located about the eddy current inspection means and positioned with a predetermined spatial registration with respect to said scanning surface for aligning the probe and maintaining uniform spacing between the workpiece surface under inspection, said eddy current alignment means having means for producing spacing-indication electrical signals in accordance with a spacing between said eddy current alignment means and said workpiece, said eddy current alignment means comprising at least three alignment eddy current elements noncollinearly positioned with respect to one another throughout said scanning surface and being mutually spaced at a predetermined distance from one another and said producing means comprising at least one .sense coil electrically interconnected in an absolute mode and being disposed in at least one layer of a multi-layer, integral structure;
    a signal processor connected to said eddy current alignment means to receive and to process said spacing-indication electrical signals, said signal processor generating data indicative of an alignment between said scanning surface and said workpiece surface in accordance with the processed electrical signals; and
    a controller connected to said signal processor to receive said alignment data, said controller being responsive to said alignment data for aligning said probe such that in operation the scanning surface thereof is aligned substantially parallel relative to said workpiece surface.

2. A system according to claim 1 wherein said inspection means comprises a plurality of inspection eddy current elements arrayed throughout said scanning surface.

3. A system according to claim 2 wherein the electrical signal producing means of each of said inspection eddy current elements comprises at least two sense coils electrically interconnected in a differential mode, said sense coils being disposed in at least one layer of said multi-layer integral structure.

4. A system according to claim 3 wherein said eddy current inspections means and said eddy current alignment means form an integral eddy current inspection probe.

5. A system according to claim 4 wherein said multi-layer structure is flexible.

6. A system according to claim 5 further comprising a housing for accommodating said flexible structure, said housing having a predetermined shape selected such that the scanning surface of said eddy current probe is conformable to a workpiece having a substantially curved surface.

7. A system according to claim 6 wherein each of said inspection eddy current elements and each of said alignment eddy current elements is respectively patterned and electrically interconnected within said flexible multi-layered structure using photolithography.

8. A system according to claim 4 wherein each of said inspection eddy current elements and each of said alignment eddy current elements is respectively patterned and electrically interconnected within said multi-layered structure using photolithography.

9. A system for providing continuous and substantially parallel alignment between a scanning surface of an inspection probe and a workpiece surface under inspection, said system comprising:
  eddy current inspection means located in a two dimensional array on said scanning surface for establishing an eddy current flow in the workpiece, a disruption in the eddy current flow therefrom representing a discontinuity, said eddy current inspection means having means for producing a respective electrical signal indicative of the discontinuity in said workpiece when positioned adjacent to said workpiece;
  eddy current alignment means located about the eddy current inspection means and positioned with a predetermined spatial registration with respect to said scanning surface for aligning the probe and maintaining uniform spacing between the workpiece surface under inspection, said eddy current alignment means having means for producing spacing-indication electrical signals in accordance with a spacing between said eddy current alignment means and said workpiece surface, said eddy current alignment means comprising at least three alignment eddy current elements noncollinearly positioned with respect to one another throughout said scanning surface and being mutually spaced at a predetermined distance from one another and said producing means comprising at least one sense coil electrically interconnected in an absolute mode and being disposed in at least one layer of a multi-layer, integral structure; and
  processing means connected to said eddy current alignment means for processing said spacing-indication electrical signals and for generating alignment data indicative of an alignment between said scanning surface and said workpiece surface in accordance with the processed electrical signals.

10. A system according to claim 9 wherein said processing means comprises at least a differential amplifier connected to said associated pair of alignment eddy current elements to receive the electrical signals produced by said associated pair, said differential amplifier generating a difference signal representing the difference of the received electrical signals and constituting at least a portion of said alignment data.

11. A system according to claim 10 and further comprising display means connected to said differential amplifier for providing visual indicia, based on said difference signal, of the alignment between at least said traversing axis and said workpiece surface.

12. A system according to claim 11 wherein each of said alignment eddy current elements is patterned and electrically interconnected within said multi-layer structure using photolithography.

13. A system according to claim 9 wherein said processing means comprises a signal processor.

14. A system according to claim 13 and further comprising a controller connected to said signal processor to receive said alignment data, said controller being responsive to said alignment data for aligning said probe such that in operation the scanning surface thereof is automatically aligned substantially parallel relative to said workpiece surface.

15. A method for establishing and maintaining continuous and substantial parallel alignment between a scanning surface of an inspection probe which in operation advances over a workpiece surface under inspection, said method comprising the steps of:
  providing a plurality of eddy current inspection elements on said scanning surface for establishing an eddy current flow in the workpiece, a disruption in the eddy current flow therefrom representing a discontinuity, and producing a respective electrical signal indicative of the discontinuity in said workpiece when positioned adjacent to said workpiece;
  providing a plurality of alignment eddy current elements located about the eddy current inspection elements and positioned with a predetermined spatial registration with respect to said scanning surface; said plurality of eddy current alignment elements comprising at least three alignment eddy current elements noncollinearly positioned with respect to one another throughout said scanning surface and being mutually spaced at a predetermined distance from one another;
  photolithographically patterning and electrically interconnecting each of said plurality of alignment eddy current elements into at least one layer of a multi-layer integral structure:
  operating each of said alignment eddy current elements in an absolute mode to produce a respective spacing-indication electrical signal in accordance with the spacing between each respective one of said eddy current elements and said workpiece surface;
  processing said electrical signals to generate data indicative of the alignment between said scanning surface and said workpiece surface; and
  aligning said probe, in accordance with said alignment data, such that in operation the scanning surface thereof is substantially parallel to said workpiece surface.

* * * * *